United States Patent
Takata

(10) Patent No.: US 10,422,988 B2
(45) Date of Patent: Sep. 24, 2019

(54) ENDOSCOPE APPARATUS

(71) Applicant: FUJIFILM Corporation, Tokyo (JP)

(72) Inventor: Takuya Takata, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 343 days.

(21) Appl. No.: 15/259,710

(22) Filed: Sep. 8, 2016

(65) Prior Publication Data

US 2016/0377855 A1    Dec. 29, 2016

Related U.S. Application Data

(63) Continuation of application No. PCT/JP2015/053887, filed on Feb. 13, 2015.

(30) Foreign Application Priority Data

Mar. 28, 2014  (JP) ................ 2014-068516

(51) Int. Cl.
| | |
|---|---|
| G02B 15/14 | (2006.01) |
| G02B 23/24 | (2006.01) |
| A61B 1/00 | (2006.01) |
| A61B 1/05 | (2006.01) |
| A61B 1/04 | (2006.01) |
| G02B 7/10 | (2006.01) |

(Continued)

(52) U.S. Cl.
CPC ...... *G02B 23/2438* (2013.01); *A61B 1/00096* (2013.01); *A61B 1/00188* (2013.01); *A61B 1/04* (2013.01); *A61B 1/045* (2013.01); *A61B 1/05* (2013.01); *G02B 7/10* (2013.01); *G02B 23/2476* (2013.01); *H04N 5/23296* (2013.01)

(58) Field of Classification Search
CPC .. G02B 23/2438; G02B 7/10; G02B 23/2476; H04N 5/23296; A61B 1/045; A61B 1/04; A61B 1/05; A61B 1/00096; A61B 1/00188
See application file for complete search history.

(56) References Cited

U.S. PATENT DOCUMENTS

2008/0239508 A1    10/2008  Guan

FOREIGN PATENT DOCUMENTS

| CN | 101276036 A | 10/2008 |
|---|---|---|
| JP | 2000-19428 A | 1/2000 |
| JP | 4127731 B2 | 7/2008 |

OTHER PUBLICATIONS

International Search Report for PCT/JP2015/053887 (PCT/ISA/210) dated May 12, 2015.

(Continued)

*Primary Examiner* — Alicia M Harrington
(74) *Attorney, Agent, or Firm* — Birch, Stewart, Kolasch & Birch, LLP

(57) ABSTRACT

An objective optical system of an observation unit of the endoscope has a zoom function, and the movable lens for changing a zoom magnification of the objective optical system is controlled to be capable of moving to only a plurality of step positions SP1 to SP4 where specific zoom magnifications are obtained. A control circuit, which controls the movable lens, considers the number N of repetitions and the duration of an on-operation of a zoom switch that instructs the movable lens to move. For example, the movable lens is moved by a step corresponding to the number N of repetitions of the on-operation, and is moved to a step position, which is provided at an end, in a case in which the duration of the on-operation is long.

21 Claims, 6 Drawing Sheets

(51) Int. Cl.
*A61B 1/045* (2006.01)
*H04N 5/232* (2006.01)

(56) References Cited

OTHER PUBLICATIONS

Written Opinion of the International Searching Authority for PCT/JP2015/053887 (PCT/ISA/237) dated May 12, 2015.
English translation of the International Preliminary Report on Patentability and Written Opinion of the International Searching Authority (Forms PCT/IB/373 and PCT/ISA/237) for International Application No. PCT/JP2015/053887, dated Oct. 4, 2016.
Chinese Office Action and Search Report dated Jul. 3, 2017, for corresponding Chinese Application No. 201580016396.1, with an English translation of the Office Action.
Extended European Search Report, dated Feb. 17, 2017, for corresponding European Application No. 15767955.6.
Chinese Second Office Action dated Nov. 28, 2017 for corresponding Chinese Application No. 201580016396.1, with an English translation.

FIG. 5

| UNIT MOVEMENT POSITION | ZOOM MAGNIFICATION | STEP POSITION |
|---|---|---|
| Pos0 | ONE TIME (NOT ENLARGED) | SP1 |
| Pos1 | | |
| Pos2 | 20 TIMES | SP2 |
| Pos3 | | |
| Pos4 | | |
| Pos5 | 40 TIMES | SP3 |
| Pos6 | | |
| Pos7 | 80 TIMES | SP4 |

ENDOSCOPE APPARATUS

CROSS-REFERENCE TO RELATED APPLICATIONS

This application is a Continuation of PCT International Application No. PCT/JP2015/053887 filed on Feb. 13, 2015, which claims priority under 35 U.S.C § 119 (a) to Japanese Patent Application No. 2014-068516 filed on Mar. 28, 2014. Each of the above application(s) is hereby expressly incorporated by reference, in its entirety, into the present application.

BACKGROUND OF THE INVENTION

1. Field of the Invention

The present invention relates to an endoscope apparatus, and more particularly, to an endoscope apparatus that controls a movable lens of an observation optical system provided in a tip portion of an endoscope insertion part.

2. Description of the Related Art

As well known, an endoscope apparatus (endoscope system) includes an endoscope (scope) that comprises an imaging section for imaging the inside of a body cavity, a processor device that performs image processing on image data taken by the imaging section of the endoscope and output from the endoscope and outputs the image data to a display device, and the like.

JJP4127731B discloses an endoscope that employs a zoom optical system of which a focal length can be changed by the movement of a part (zoom lens) of the lenses in the direction of an optical axis as an objective optical system of an imaging section of an endoscope and can change the magnification (zoom magnification) of an observation image taken by the imaging section.

According to JP4127731B, the endoscope includes a zoom switch that is used by a user to instruct the zoom magnification of the observation image to be changed, and the zoom switch includes a wide-side switch that instructs the zoom magnification to be changed to a wide side (a low-magnification side), and a telephoto-side switch that instructs the zoom magnification to be changed to a telephoto-side (a high-magnification side).

The zoom lens of the zoom optical system is moved to the wide side or the telephoto side by a predetermined distance when drive pulses are supplied to an actuator connected to the zoom lens, and the position of the zoom lens is controlled by the number of drive pulses supplied to the actuator. Further, JP4127731B discloses that various modes are provided for the control of the zoom lens, drive pulses of which the number is predetermined are supplied to the actuator in a user's on-operation of the telephoto-side switch or the wide-side switch of the zoom switch in a step mode that is one among the modes, and the zoom lens is moved to a position where a predetermined specific zoom magnification (one time, 20 times, 40 times, 60 times, . . . ) is obtained.

SUMMARY OF THE INVENTION

A so-called step zoom function, which limits changeable zoom magnifications to magnifications corresponding to several steps so that the zoom magnification can be changed by step in the above-mentioned step mode disclosed in JP4127731B, is a function that is convenient for a user that is satisfied by only major changes of the zoom magnification without requiring minor changes of the zoom magnification since the number of times of operation of the zoom switch or the operation time of the zoom switch can be reduced.

The step mode of JP4127731B further includes several modes. Whenever the telephoto-side switch of the zoom switch is turned on once for the zoom magnifications (for example, one time, 20 times, 40 times, 60 times, 80 times, and 100 times) corresponding to, for example, a plurality of steps, the zoom magnification is increased by one step (one time 20 times→40 times . . . ). When the wide-side switch is turned on once, the zoom magnification returns to one time.

For this reason, for example, in a case in which a user wants to increase a zoom magnification by two steps, the user waits for the increase of a zoom magnification by one step after turning on the telephoto-side switch once and then needs to turn on the telephoto-side switch once again. Further, in a case in which a user wants to reduce a zoom magnification, the user may have to turn on the telephoto-side switch until a zoom magnification becomes a desired zoom magnification after turning on the wide-side switch once to set a zoom magnification to one time.

Accordingly, the operability of an operation in a case, in which a zoom magnification is changed by a plurality of steps, or the like is not sufficiently considered. Further, in an objective optical system of an imaging section, which includes a movable lens for the adjustment of a focus or the like without being limited to the operation of a zoom magnification, it is preferable that operability in a case in which the movable lens can be moved so as to be limited to a plurality of step positions is also improved likewise.

The invention has been made in consideration of the above-mentioned circumstances, and an object of the invention is to provide an endoscope apparatus that improves operability in a case in which a movable lens of an objective optical system of an imaging section of an endoscope is moved to a plurality of predetermined step positions.

In order to achieve the object, an endoscope apparatus according to an aspect of the invention comprises: a movable lens that forms an objective optical system of an endoscope; a lens drive unit that electrically drives the lens; an operating unit that outputs operation signals corresponding to an on-operation and an off-operation of an operator; and a lens control unit that moves the lens to one step position among a plurality of step positions, detects the duration of the on-operation, which is obtained when the on-operation is performed, and the number of repetitions of the on-operation, which is obtained when the on-operation and the off-operation are continuously repeated, on the basis of the operation signal, and determining a step position to which the lens is to be moved on the basis of the detected duration of the on-operation and the detected number of repetitions of the on-operation.

According to this aspect, even though the operating unit is simple a unit that has only an on-operation and an off-operation, it is possible to perform various operations in consideration of the duration and the number of repetitions of an on-operation. Accordingly, not only a simple operation for moving the movable lens to the plurality of step positions by one step but also advanced operations, such as the movement of the movable lens corresponding to a plurality of steps, the movement of the movable lens to an end, and the return of the movable lens to an original position, can be performed without an increase of the number of operating unit.

In the endoscope apparatus according to the aspect of the invention, if the on-operation is performed when the on-operation, which is performed after the duration of the off-operation becomes equal to or longer than a threshold T1, is defined as a first on-operation, the number of repetitions of the on-operation is defined as 1, and the duration of the off-operation performed after the on-operation is shorter than the threshold T1, it is preferable that the lens control unit increases the number of repetitions of the on-operation by 1.

According to this aspect, it is easy to distinguish an operator's on-operation for intuitively increasing the number of repetitions from a single on-operation and to perform the on-operation and the single on-operation.

In the endoscope apparatus according to the aspect of the invention, when the lens control unit detects the first on-operation at the time of stopping of the lens, it is preferable that the lens control unit moves the lens to a step position spaced apart from a step position, which is obtained when the lens is stopped, in a moving direction, which is predetermined so as to correspond to the operating unit, by a step corresponding to the number of repetitions of the on-operation including the detected first on-operation after starting to move the lens in the moving direction.

According to this aspect, the lens is not moved by the plurality of steps through the on-operation of the operating unit, which is performed whenever the lens is moved by one step, and it is possible to move the lens by the plurality of steps through one continuous on-operation.

In the endoscope apparatus according to the aspect of the invention, when the lens control unit detects the first on-operation at the time of stopping of the lens, it is preferable that the lens control unit moves the lens to a step position that is provided at an end in a moving direction predetermined so as to correspond to the operating unit by the detection of the first on-operation after starting to move the lens in the moving direction in a case in which the duration of the first on-operation becomes equal to or longer than a threshold T2.

According to this aspect, it is possible to move the lens to a step position, which is provided at an end, by performing only an on-operation having long duration, that is, a so-called long push operation.

In the endoscope apparatus according to the aspect of the invention, if the lens control unit detects the first on-operation when moving the lens in the moving direction that is predetermined so as to correspond to the operating unit, it is preferable that the lens control unit moves the lens to a step position that is provided at an end in the moving direction.

According to this aspect, even if the lens is moved to a step position other than the step position provided at the end, it is possible to easily switch the movement of the lens to the movement of the lens to the step position that is provided at the end.

It is preferable that the endoscope apparatus according to the aspect of the invention further comprises a reverse operating unit outputs operation signals corresponding to an on-operation and an off-operation of an operator. If the lens control unit detects an on-operation performed by the reverse operating unit when moving the lens in a moving direction that is predetermined so as to correspond to the operating unit, it is preferable that the lens control unit moves the lens to a step position that is obtained at the time of the start of the movement of the lens.

According to this aspect, when the lens is moved to another step position from a predetermined step position, it is possible to easily return the lens to an original step position.

It is preferable that the endoscope apparatus according to the aspect of the invention further comprises a reverse operating unit that outputs operation signals corresponding to an on-operation and an off-operation of an operator. If the lens control unit detects an on-operation performed by the reverse operating unit when moving the lens in a moving direction, which is predetermined so as to correspond to the operating unit, to move the lens to a target step position, it is preferable that the lens control unit moves the lens to a step position, which is spaced apart from a target position in a direction opposite to the moving direction by one step, after moving the lens to the target step position.

According to this aspect, when the lens is moved to a predetermined step position, it is possible to instruct the lens to return to a step position in an opposite direction by one step before the lens reaches the step position.

It is preferable that the endoscope apparatus according to the aspect of the invention further comprises a reverse operating unit that outputs operation signals corresponding to an on-operation and an off-operation of an operator. If the lens control unit detects an on-operation performed by the reverse operating unit when moving the lens in a moving direction, which is predetermined so as to correspond to the operating unit, to move the lens to a target step position, it is preferable that the lens control unit moves the lens to a step position closest to a position of the lens, which is obtained at the time of the detection of the on-operation performed by the reverse operating unit, in a direction opposite to the moving direction.

According to this aspect, when the lens is being moved to a predetermined step position, it is possible to instruct the lens to move to another step position.

In the endoscope apparatus according to the aspect of the invention, it is preferable that the lens drive unit is a unit that drives the lens by a DC motor.

According to this aspect, the size of the lens drive unit can be reduced, which contributes to reduction of the size of the endoscope.

In the endoscope apparatus according to the aspect of the invention, it is preferable that the operating unit is a unit that outputs an operation signal corresponding to an operation for pushing a switch as the on-operation.

In the endoscope apparatus according to the aspect of the invention, it is preferable that the lens control unit includes a lookup table in which the step positions are associated with positions that are settable when the lens control unit moves the lens by a moving distance corresponding to the minimum unit by a drive instruction given to the lens drive unit, and moves the lens to a target step position with reference to the lookup table.

In the endoscope apparatus according to the aspect of the invention, it is preferable that the lens is a lens for a variable zoom magnification of the objective optical system and the step position is a position of the lens for the setting of a predetermined zoom magnification.

According to the invention, it is possible to improve operability in a case in which a movable lens of an objective optical system of an imaging section of an endoscope is moved to a plurality of predetermined step positions.

BRIEF DESCRIPTION OF THE DRAWINGS

FIG. 5 is a diagram that is used to illustrate a correspondence relationship between unit movement positions Pos0 to Pos7 and step positions SP1 to SP4.

Figure 6:
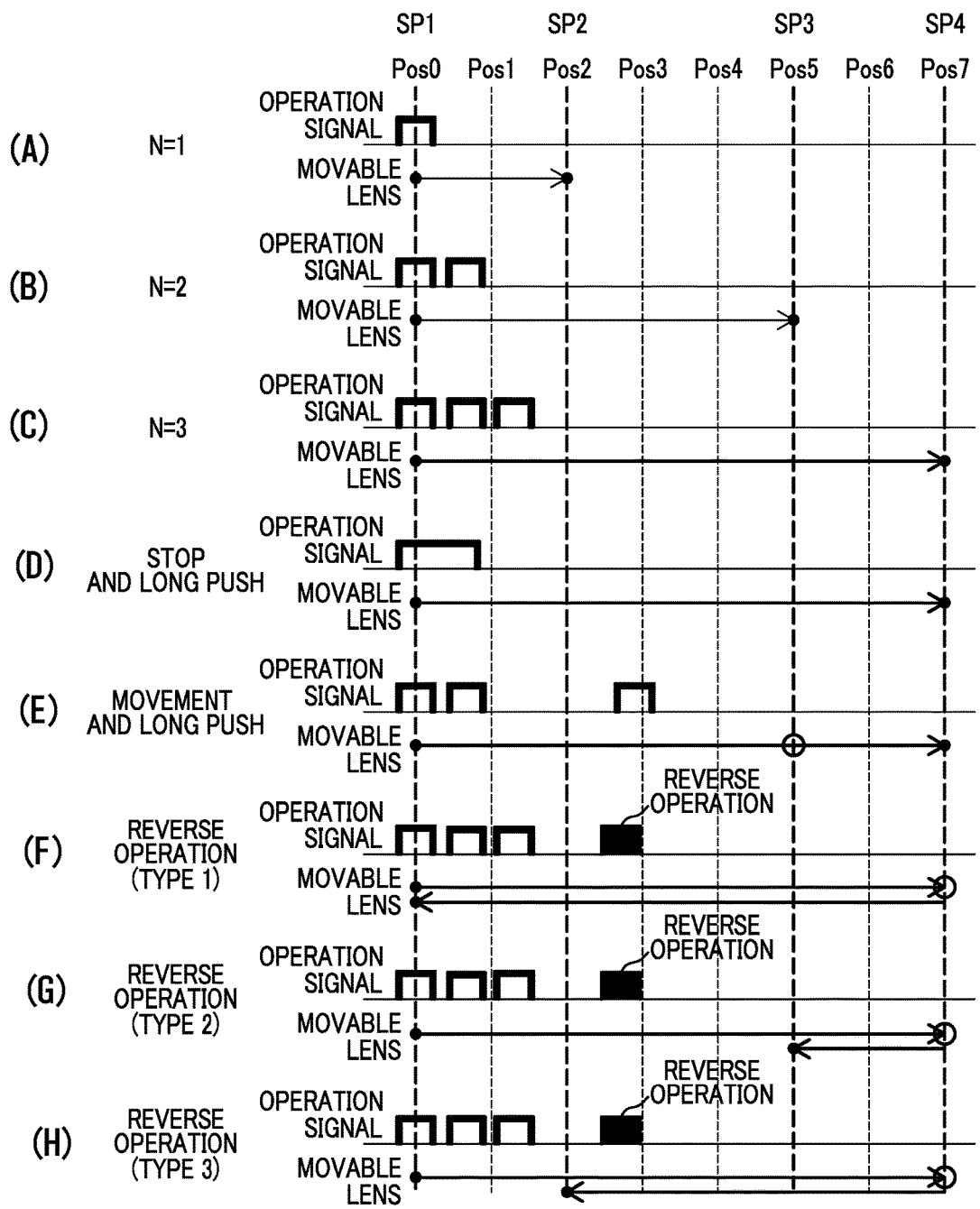

Parts (A) to (H) of FIG. 6 are diagrams showing the movement modes of a movable lens based on the number N of repetitions and the duration T of an on-operation of a telephoto-side switch.

DESCRIPTION OF THE PREFERRED EMBODIMENTS

A preferred embodiment of the invention will be described in detail below with reference to the accompanying drawings.

Figure 1:
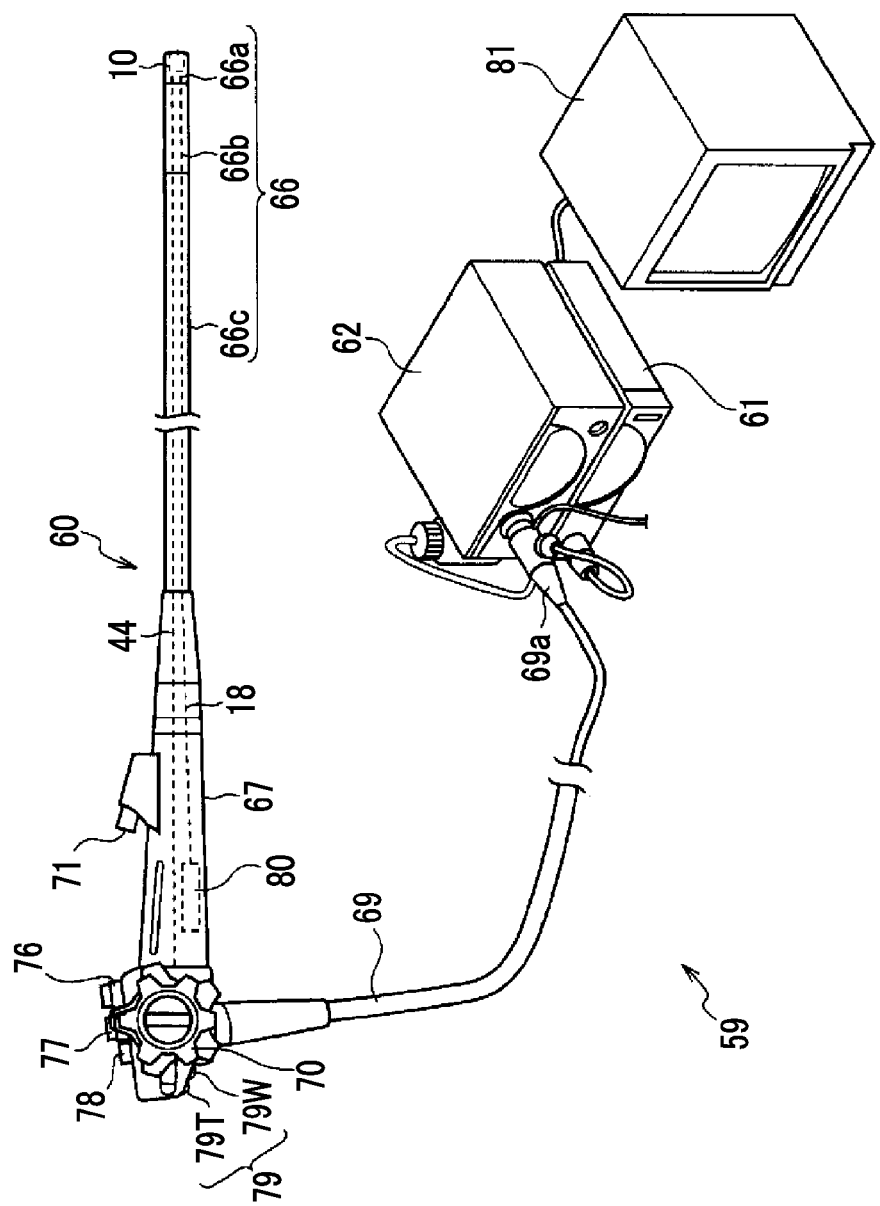
FIG. 1 is a perspective view showing the structure of an endoscope system that is an embodiment of an endoscope apparatus according to the invention.

FIG. 1 is a perspective view showing the structure of an endoscope system that is an embodiment of an endoscope apparatus according to the invention.

An endoscope system 59 shown in FIG. 1 includes an endoscope 60 (electronic endoscope), a processor device 61, and a light source device 62. The endoscope 60 includes a flexible insertion part 66 that is inserted into a patient's body cavity, a hand operation unit 67 that is connected to a base end portion of the insertion part 66, a connector 69a that is connected to the processor device 61 and the light source device 62, and a universal cord 69 that connects the hand operation unit 67 to the connector 69a.

The insertion part 66 includes a tip portion 66a, a bendable portion 66b, and a soft portion 66c in this order from a tip. The tip portion 66a is made of a hard resin, and is provided with an imaging section 10 of which the detail will be described below.

The bendable portion 66b is bent up and down and left and right by the rotation of an angle knob 70 of the hand operation unit 67, and changes the direction of the tip portion 66a. The soft portion 66c has flexibility, and connects the bendable portion 66b to the hand operation unit 67 in a long shape.

Figure 2:
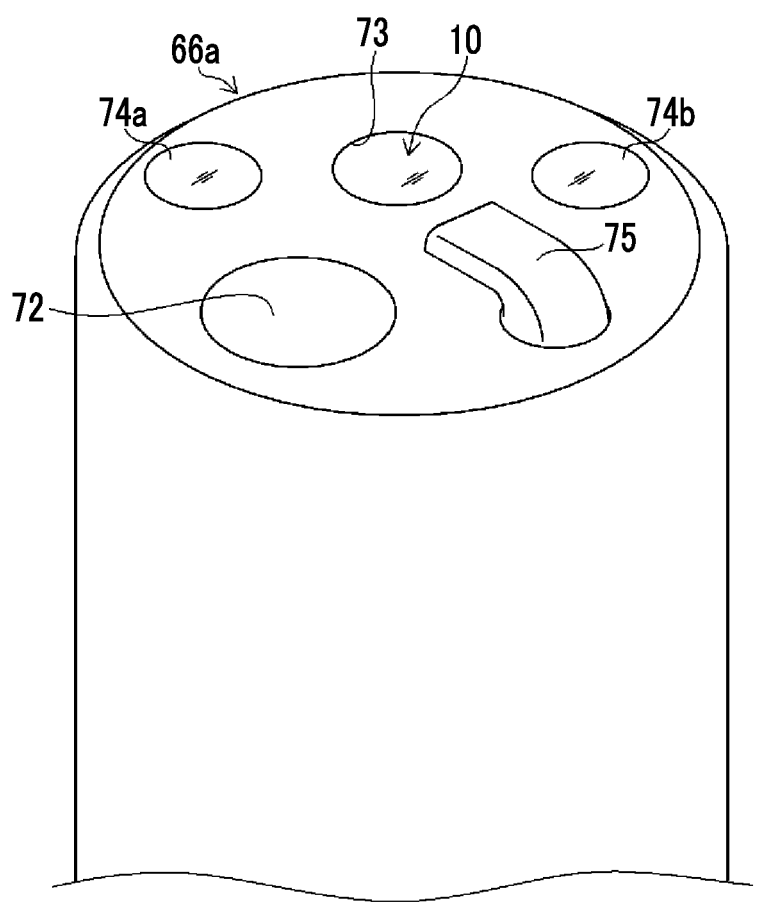
FIG. 2 is a perspective view showing an end face of an insertion part of an endoscope.

Further, a forceps outlet 72 that guides a treatment tool such as forceps, an observation window 73 through which the image light of a portion to be observed enters the imaging section 10, illumination windows 74a and 74b through which the portion to be observed is irradiated with illumination light, and an air supply/water supply nozzle 75 that ejects water or air washing and drying the observation window 73 are provided on an end face of the insertion part 66 (the tip portion 66a) as shown in FIG. 2.

The hand operation unit 67 of FIG. 1 is provided with various operation members, such as an air supply/water supply button 76, a suction button 77, a release button 78, and a zoom switch 79, in addition to the angle knob 70. It is possible to eject water or air from the air supply/water supply nozzle 75 of the end face of the insertion part 66 by pressing the air supply/water supply button 76 and to suck objects to be sucked, such as fluid and tissue in the body, from the forceps outlet 72 of the end face of the insertion part 66 by pressing the suction button 77. The forceps outlet 72 communicates with a forceps port 71 of the hand operation unit 67 through the inside of the insertion part 66 and a treatment tool, such as forceps, which is inserted from the forceps port 71, is guided by the forceps outlet 72.

Further, it is possible to record an observation image, which is taken by the imaging section 10, in the form of a still image by pressing the release button 78, and to change the zoom magnification of the imaging section 10 by pushing (pressing) the zoom switch 79.

The processor device 61 is electrically connected to the light source device 62, and generally controls the operation of the endoscope system 59. The processor device 61 supplies power to the endoscope 60 through the universal cord 69 and a transmission cable 44 inserted into the insertion part 66, and controls the drive of the imaging section 10 of the tip portion 66a. Furthermore, the processor device 61 receives signals from the imaging section 10 through the transmission cable 44, and generates image data by performing various kinds of processing. A monitor 81 is connected to the processor device 61. The monitor 81 displays an observation image on the basis of the image data generated from the processor device 61.

Figure 3:
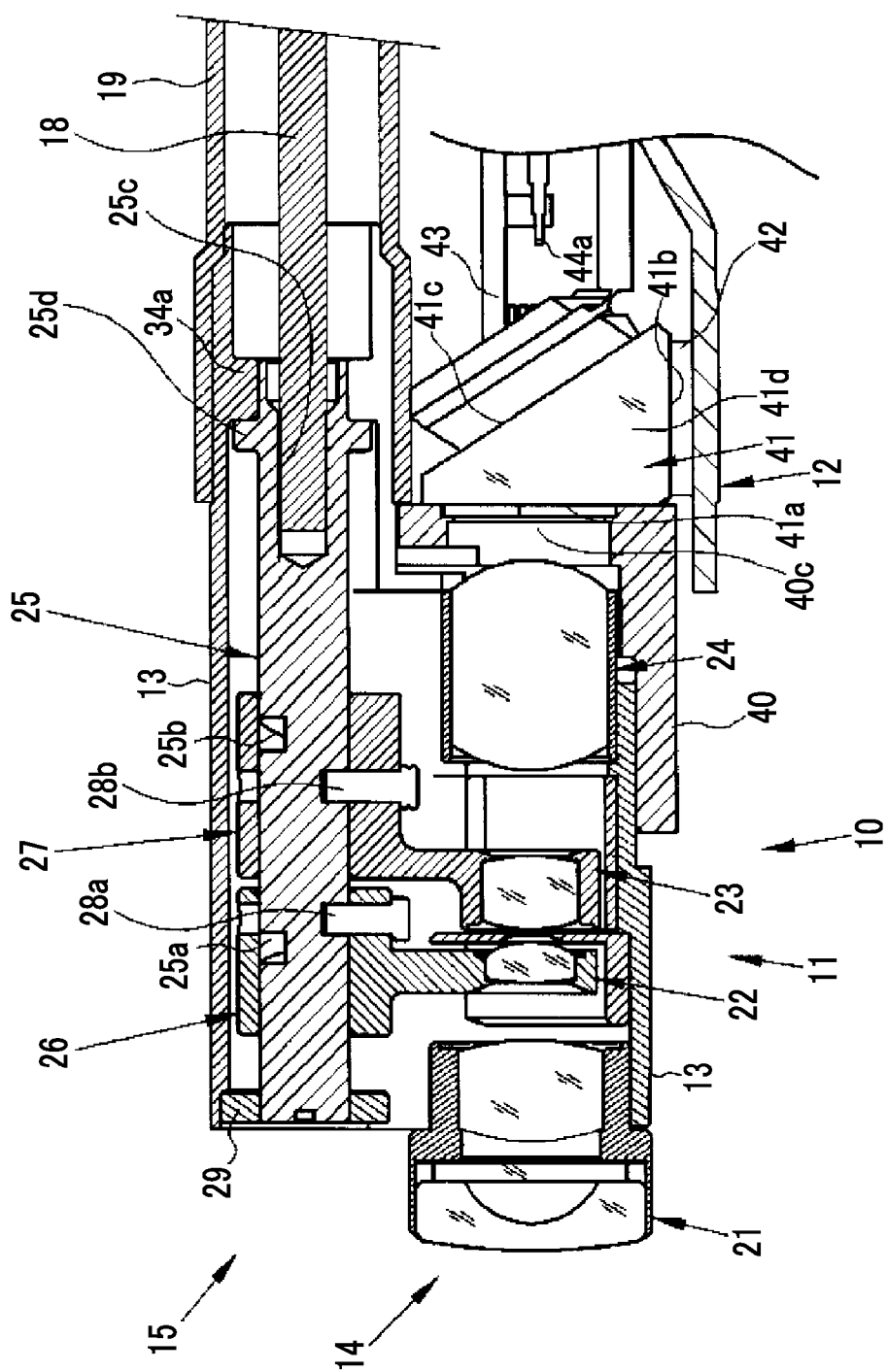
FIG. 3 is a sectional view of an imaging section that is received and disposed in a tip portion of the endoscope.

Next, the structure of the imaging section 10, which is provided in the tip portion 66a of the endoscope 60, will be described. FIG. 3 is a sectional view of the imaging section 10 that is received and disposed in the tip portion 66a.

As shown in FIG. 3, the imaging section 10 includes an imaging lens unit 11 and an image pickup unit 12.

The imaging lens unit 11 includes a lens moving unit 15 and an imaging lens 14 of an objective optical system of the imaging section 10.

The imaging lens 14 includes a first stationary lens 21, a first movable lens 22, a second movable lens 23, and a second stationary lens 24 that are disposed in this order in the direction of an optical axis. The stationary lenses 21 and 24 are held by a holding frame, and are fixed to a housing 13 that integrally receives and holds the imaging lens unit 11.

The lens moving unit 15 comprises a camshaft 25, and a first lens moving frame 26 and a second lens moving frame 27 that slide on the camshaft 25. The lens moving unit 15 can change the focal length of the imaging lens 14 by moving the movable lenses 22 and 23 in the direction of the optical axis so that imaging can be performed with a variable magnification.

The camshaft 25 includes two cam grooves 25a and 25b that are formed on the outer peripheral surface thereof, a wire connection hole 25c that is formed at the rear end thereof along the axis thereof, and a locking flange 25d that is formed on the outer peripheral surface of the rear end portion thereof. An end of a wire 18 for rotary drive is fixed to the wire connection hole 25c. The wire 18 is inserted into a protective tube 19 and is connected to a motor 80 (see FIG. 1) that is provided in the hand operation unit 67. The drive of the motor 80 is controlled by the operation of the zoom switch 79 of the hand operation unit 67 so that the motor 80 is driven in a normal direction or a reverse direction.

A retaining ring 29 is mounted on the tip of the camshaft 25. The camshaft 25 is rotatably supported by the retaining ring 29. Further, the locking flange 25d, which is formed on the rear end portion of the camshaft 25, is locked to a locking ring 34a, so that the axial movement of the camshaft 25 is regulated.

The first lens moving frame 26 is a lens frame and holds the first movable lens 22, and the camshaft 25 is inserted into the first lens moving frame 26. The second lens moving frame 27 is also a lens frame and holds the second movable lens 23, and the camshaft 25 is inserted into the second lens moving frame 27.

A first engagement pin 28a is mounted on the first lens moving frame 26, and an end of the engagement pin 28a is fitted to the first cam groove 25a. Furthermore, an engagement pin 28b is mounted on the second lens moving frame 27, and the second engagement pin 28b is fitted to the second cam groove 25b.

When the camshaft 25 is rotated in a normal direction or a reverse direction by the motor 80 (see FIG. 1), the camshaft 25 is rotationally displaced according to the rotation angle of the camshaft 25 and the first and second lens moving frames 26 and 27 are moved together with the first and second movable lenses 22 and 23 in the direction of the optical axis through the respective engagement pins 28a and 28b by the rotational displacement of the camshaft 25.

Accordingly, the first and second movable lenses 22 and 23 have a positional relationship defined by the cam grooves 25a and 25b and are moved in the direction of the optical axis, so that the focal length of the imaging lens 14, that is, the zoom magnification of the imaging section 10 is changed.

The image pickup unit 12 is mounted on the rear end of the imaging lens 14 of the imaging lens unit 11.

The image pickup unit 12 includes a prism holding frame 40, a prism 41, a solid image pickup element 42, and the like.

The prism 41 is a rectangular prism, and includes five surfaces, that is, an incident surface 41a and a light-emitting surface 41b that cross each other at a right angle, a reflective surface 41c that is formed of an inclined surface, and both side surfaces 41d. The prism 41 is held by the prism holding frame 40 that is fixed to the housing 13 of the imaging lens unit 11.

An opening portion 40c through which light incident from the imaging lens 14 passes is formed at the rear end portion of the prism holding frame 40, the incident surface 41a of the prism 41 is disposed along the rear end face of the prism holding frame 40, and the light-emitting surface 41b of the prism 41 is disposed so as to be orthogonal to the incident surface 41a.

The solid image pickup element 42 is mounted on the light-emitting surface 41b of the prism 41, and a circuit board 43 for driving the solid image pickup element 42 is mounted on the inclined surface of the prism 41 by an adhesive. The universal cord 69 and a wire (signal wire) 44a of the transmission cable, which is inserted into the insertion part 66, are connected to the circuit board 43.

The solid image pickup element 42 is a CCD (Charge Coupled Device) type or a CMOS (Complementary Metal Oxide Semiconductor) type solid image pickup element. After passing through the imaging lens 14 and being reflected by the prism 41, image light from a portion to be observed is incident on the image pickup surface of the solid image pickup element 42. The solid image pickup element 42 picks up the light image of the portion to be observed, which is formed on the image pickup surface, and outputs the light image as an image pickup signal.

The structure of the imaging section 10 shown in FIG. 3 is illustrative, and the imaging section 10 is not limited thereto.

Figure 4:
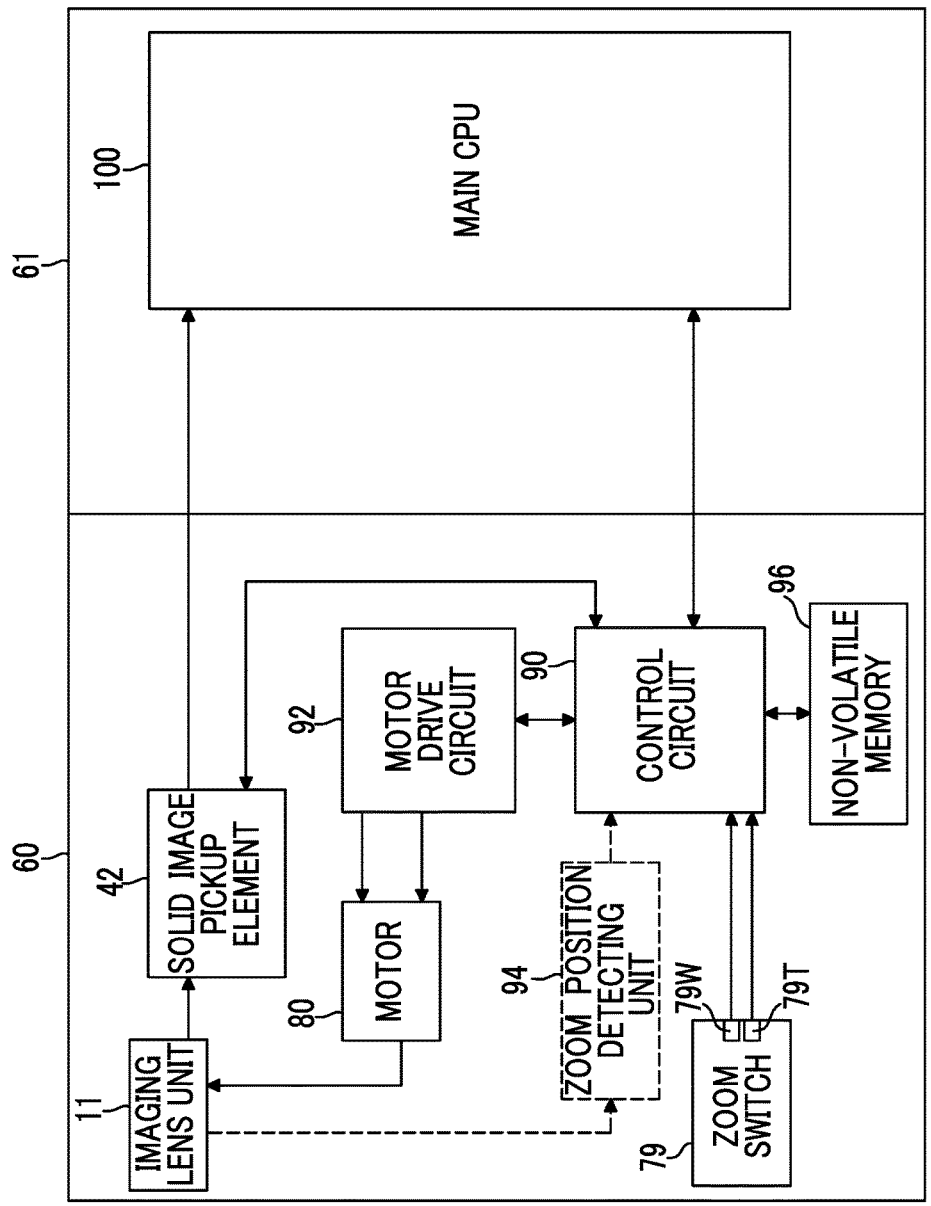
FIG. 4 is a block diagram showing components that are mainly associated with the control of an imaging lens unit in the endoscope system.

FIG. 4 is a block diagram showing components that are mainly associated with the control of the imaging lens unit 11 in the endoscope system 59.

As shown in FIG. 4, the endoscope 60 comprises a control circuit 90 as a lens control unit, and the motor 80 (see FIG. 1) moving the first and second movable lenses 22 and 23 of the above-mentioned imaging lens unit 11, that is, the motor 80 rotating the camshaft 25 is adapted to be controlled by the control circuit 90 through a motor drive circuit 92 serving as a lens drive unit.

The first and second movable lenses 22 and 23, which are movable lenses of the objective optical system, are generically referred to as a movable lens, and the states of the positions of the first and second movable lenses 22 and 23, which are determined by the combination of the positions of the first and second movable lenses 22 and 23, are referred to as the positions of the movable lens. Specifically, the position of the movable lens can be expressed by the rotational position of the camshaft 25. For example, a zoom position detecting unit 94, which is shown in FIG. 4, detects the rotational position of the camshaft 25 and provides information about the detected rotational position to the control circuit 90 as information that represents the position of the movable lens.

Further, the control circuit 90 also controls the solid image pickup element 42 and the like of the imaging section 10, and generally controls the entire endoscope 60. The image pickup signal, which is output from the solid image pickup element 42, is transmitted to the processor device 61, and is subjected to various kinds of processing by a main CPU 100 and the like of the processor device 61.

The motor 80 is, for example, a DC motor that is advantageous for the reduction of size, and is driven by a drive signal transmitted from the motor drive circuit 92.

The motor drive circuit 92 continues transmitting a voltage signal having a predetermined constant voltage or a voltage signal having a specific waveform (for example, a pulse train) to the motor 80 during the output time of a drive signal designated by the control circuit 90 (or while a drive signal is instructed to be output). Accordingly, the movable lens is moved. It is possible to drive the motor 80 in a normal direction or a reverse direction by reversing the polarity of the drive signal between a positive polarity and a negative polarity, and to move the movable lens to both a wide side (wide angle side) and a telephoto side (expansion side).

The control circuit 90 gives a drive instruction about the moving direction of the movable lens, that is, the polarity of the drive signal, which is transmitted to the motor 80, and the output time of the drive signal to the motor drive circuit 92. The control circuit 90 may give an instruction, which allows a drive signal to continue being output, to the motor drive circuit 92 during the output time, instead of giving an instruction about the output time of the drive signal to the motor drive circuit 92.

Here, the position of the movable lens is controlled by the output time of the drive signal, which is supplied to the motor 80, and the minimum output time (minimum output time) is predetermined as the output time. First, the position of the movable lens, which is obtained when the movable lens is set to a wide end (an end close to the wide side in the moving direction), is denoted by Pos0. In this case, the control circuit 90 instructs the motor drive circuit 92 while setting the moving direction of the movable lens to the telephoto side and setting the output time of the drive signal to the minimum output time. Accordingly, a drive signal is transmitted to the motor 80 from the motor drive circuit 92. In this case, the movable lens is moved by a moving distance as the minimum unit (unit moving distance) and is stopped. In a case in which the movable lens is moved to the telephoto side by the unit moving distance in this way, the movable lens is set to a plurality of positions until the movable lens reaches a telephoto end (an end close to the telephoto side in the moving direction). When these positions are positions, which can be set by the movement of the movable lens corresponding to the minimum unit, and are referred to as unit movement positions, the unit movement positions are set to eight points Pos0 to Pos7 in this embodiment. In this case, Pos0 denotes the position of the wide end, and Pos7 denotes the position of the telephoto end.

Meanwhile, the zoom switch 79, which is an embodiment of operating unit for operating zoom, is connected to the control circuit 90, and the control circuit 90 determines a target position to which the movable lens is to be moved on the basis of an operation signal transmitted from the zoom switch 79 and gives the above-mentioned instruction to the motor drive circuit 92 so that the movable lens is moved to the target position.

The hand operation unit 67 of the endoscope 60 is provided with the zoom switch 79 as shown in FIG. 1. The zoom switch 79 includes a wide-side switch 79W that instructs the zoom magnification of the observation image, which is taken by the imaging section 10, to be changed to the wide side (low-magnification side) and a telephoto-side switch 79T that instructs the zoom magnification of the observation image to be changed to the telephoto side (high-magnification side). When pressed, each of the wide-side switch 79W and the telephoto-side switch 79T is subjected to an on-operation and transmits an operation signal, which corresponds to the on-operation, (a high-level voltage signal in this embodiment) to the control circuit 90. When not pressed, each of the wide-side switch 79W and the telephoto-side switch 79T is subjected to an off-operation and transmits an operation signal, which corresponds to the off-operation, (a low-level voltage signal in this embodiment).

The control circuit 90 is connected to the main CPU 100 of the processor device 61, and can transmit and receive various signals. Accordingly, the same operation signals as the zoom switch 79 can be transmitted to the control circuit 90 by the main CPU 100, and the motor drive circuit 92 can also be instructed to be driven on the basis of the operation signals. For example, a operating unit, such as a zoom switch (foot switch) operated by a foot, can be connected to the processor device 61, and an operation signal of the operating unit can be transmitted to the control circuit 90 through the main CPU 100.

The control circuit 90 determines the target position to which the movable lens is to be moved on the basis of the operation signals transmitted from the zoom switch 79, but determines step positions, which do not corresponds to the above-mentioned unit movement positions Pos0 to Pos7 but corresponds to specific zoom magnifications, as the target position.

FIG. 5 illustrates a correspondence relationship between the unit movement positions Pos0 to Pos7 and step positions SP1 to SP4.

As shown in FIG. 5, four positions SP1 to SP4 are determined as the step positions in this embodiment, and the step position SP1 is the position of the movable lens when the zoom magnification is 1 and corresponds to the position of the unit movement position Pos0. The step position SP2 is the position of the movable lens when the zoom magnification is 20, and corresponds to the position of the unit movement position Pos2. The step position SP3 is the position of the movable lens when the zoom magnification is 40, and corresponds to the position of the unit movement position Pos5. The step position SP4 is the position of the movable lens when the zoom magnification is 80, and corresponds to the position of the unit movement position Pos7.

As described above, the step positions SP1 to SP4 correspond to cases in which the zoom magnification is 1 (the observation image is not enlarged), 20, 40, and 80, respectively, and also correspond to the unit movement positions Pos0, Pos2, Pos5, and Pos7. Accordingly, when a high-level voltage signal, which represents that the telephoto-side switch 79T is subjected to the on-operation one time, is transmitted to the control circuit 90, the control circuit 90 determines a step position, which is distant toward the telephoto side from the step position where the movable lens is set at present by one step, as the target position (target step position). For example, when the current step position is SP2, the control circuit 90 determines SP3 as the target step position.

Further, when a high-level voltage signal, which represents that the wide-side switch 79W is subjected to the on-operation one time, is transmitted to the control circuit 90, the control circuit 90 determines a step position, which is distant toward the wide side from the step position where the movable lens is set at present by one step, as the target step position. For example, when the current step position is SP2, the control circuit 90 determines SP1 as the target step position.

When determining the target step position in this way, the control circuit 90 reads out a lookup table, in which the step positions SP1 to SP4 are associated with the unit movement positions Pos0 to Pos7 as shown in FIG. 5, from a non-volatile memory 96 shown in FIG. 4 and calculates the moving direction of the movable lens to the target step position and the moving distance of the movable lens until the target step position with reference to the lookup table.

The moving distance of the movable lens until the target step position is calculated as a multiple of the above-mentioned unit moving distance. The value of the multiple corresponds to the number of times of change of the unit movement position between a unit movement position, which corresponds to the current step position, and the unit movement position that corresponds to the target step position. For example, when the current step position is SP2 and the target step position is SP3, the unit movement position corresponding to the current step position SP2 is Pos2 and the unit movement position corresponding to the target step position SP3 is Pos5. Accordingly, the number of times of change of the unit movement position until the target step position is 3 (=5−2) and the moving distance of the movable lens is three times the unit moving distance. Therefore, the multiple is 3.

Further, the control circuit 90 gives the drive instruction about the moving direction of the movable lens and the output time of the drive signal to the motor drive circuit 92 as described above. The output time of the drive signal is a value that is obtained by multiplying the minimum output time, which is required to move the movable lens by the unit moving distance, by the multiple that is calculated as described above (the number of times of change of the unit movement position until the target step position).

Accordingly, when the motor drive circuit 92 transmits the drive signal to the motor 80, the movable lens is moved to the target step position and is stopped.

An embodiment about an instruction that is based on the target step position determined by the control circuit 90 and is given to the motor drive circuit 92 as described above and the drive of the movable lens, which is based on the instruction and is performed by the motor drive circuit 92, is illustrative, and processing and control for moving the movable lens to the target step position are not limited to the above-mentioned embodiment.

Next, a specific embodiment of the determination of the target step position, which is performed by the control circuit 90 and is based on the operation of the zoom switch 79, will be described.

The operation of the telephoto-side switch 79T of the telephoto-side switch 79T and the wide-side switch 79W of the zoom switch 79 will be mainly described in the following description. Since the operation of the telephoto-side switch 79T and the operation of the wide-side switch 79W are not different from each other except that the moving direction of the movable lens is reversed in a case in which the telephoto-side switch 79T is operated, the description of the operation of the wide-side switch 79W will be omitted.

First, the control circuit 90 measures the duration T and the number N of repetitions of an on-when the telephoto-side switch 79T is subjected to the on-operation. The control circuit 90 measures the duration T and the number N of repetitions of an on-operation when the telephoto-side switch 79T is subjected to the on-operation.

The duration T of the on-operation is a time while the on-operation of the telephoto-side switch 79T (a state in which the telephoto-side switch 79T is pressed) for one time continues, and means a time while a high-level voltage signal continues to be transmitted from the telephoto-side switch 79T. When the duration T of an on-operation is shorter than a predetermined threshold T2, the on-operation is distinguished as a normal on-operation. When the duration T of an on-operation is equal to or longer than the threshold T2, the on-operation is distinguished as a long push on-operation.

If an on-operation is performed when an on-operation, which is performed after the duration of an off-operation of the telephoto-side switch 79T (a state in which the telephoto-side switch 79T is not pressed) becomes equal to or longer than a predetermined threshold T1, is defined as a first on-operation, the number N of repetitions of the on-operation at that time is defined as 1, and the duration of an off-operation performed after a predetermined on-operation is shorter than the threshold T1, the above-mentioned number N of repetitions means the number N of repetitions that is obtained by increasing the number N of repetitions of the on-operation by 1.

For example, if the operation is switched to an off-operation after the first on-operation is performed and an on-operation is performed again when the duration of the off-operation is shorter than a threshold T1, the number N of repetitions of the on-operation is 2. When the same operation is further performed, the number N of repetitions becomes 3. If the duration of an off-operation after the first, second, or third on-operation becomes equal to or longer than the threshold T1, an on-operation performed first thereafter is the first on-operation and the number N of repetitions is 1.

Schematically, the number N of repetitions of the on-operation means the number of on-operations that are repeated when the on-operation of the telephoto-side switch 79T is repeated for a short period.

FIGS. 6(A) to 6(H) are diagrams illustrating modes in which the movable lens is moved to a target step position determined according to the number N of repetitions and the duration T of the on-operation of the telephoto-side switch 79T and modes of the movement of the movable lens when the on-operation of the wide-side switch 79W (reverse operation) is performed during the movement of the movable lens to the telephoto side.

A case in which the number N of repetitions of the on-operation of the telephoto-side switch 79T is 1 and a normal on-operation is performed will be described first. As shown in FIG. 6(A), the current step position of the movable lens is SP1 (the unit movement position Pos0) and is stopped. At this time, it is regarded that the telephoto-side switch 79T is subjected to a normal on-operation, which has duration T shorter than a threshold T2, as the first on-operation. Then, repeated on-operations are not performed and the number N of repetitions becomes 1.

In this case, when detecting the first on-operation (the high-level voltage signal), the control circuit 90 sets the number N of repetitions to 1 at that time. Then, the control circuit 90 determines the step position SP2 (the unit movement position Pos2), which is close to the telephoto side from the current step position SP1 by one step corresponding to the number N of repetitions, as the target step position. When the control circuit 90 determines the step position SP2 as the target step position, the control circuit 90 instructs the motor drive circuit 92 to move the movable lens to the target step position SP2 without waiting for the ending of the first on-operation. When the control circuit 90 confirms that the duration T of the first on-operation is shorter than the threshold T2, the control circuit 90 does not apply the following change to the target step position. Accordingly, the movable lens is moved to the step position SP2 and is stopped as shown in part (A) of FIG. 6.

Also in cases in which the current step position of the movable lens is SP2 and SP3, the movable lens is moved to the step position, which is close to the telephoto side by one step, by the same normal on-operation. However, since a step position closer to the telephoto side than SP4 is not present in a case in which the current step position of the movable lens is set to SP4 that is provided at the telephoto end (the unit movement position Pos7), the on-operation of the telephoto-side switch 79T is ineffective. Accordingly, the movable lens is not moved. An on-operation for setting the step position, which is also not present in another aspect of the on-operation of the zoom switch 79 to be described below, as the target step position is ineffective even though not particularly described.

According to the operation described with reference to part (A) of FIG. 6, it is possible to move the movable lens to the telephoto side by one step.

Next, a case in which the number N of repetitions of the on-operation of the telephoto-side switch 79T is 1 and a long push on-operation is performed will be described. As shown in part (D) of FIG. 6, the current step position of the movable lens is SP1 (the unit movement position Pos0) and is stopped. At this time, it is regarded that the telephoto-side switch 79T is subjected to a long push on-operation, which has duration T equal to or longer than the threshold T2, as the first on-operation. Then, repeated on-operations are not performed and the number N of repetitions becomes 1.

In this case, when detecting the first on-operation, the control circuit 90 sets the number N of repetitions to 1 at that time. Then, the control circuit 90 determines the step position SP2 (the unit movement position Pos2), which is close to the telephoto side from the current step position SP1 by one step corresponding to the number N of repetitions, as the target step position. When the control circuit 90 determines the step position SP2 as the target step position, the control circuit 90 instructs the motor drive circuit 92 to move the movable lens to the target step position SP2 without waiting for the ending of the first on-operation.

When the control circuit 90 confirms that the duration T of the first on-operation is equal to or longer than the threshold T2, the control circuit 90 changes the target step position to SP4, which is provided at the telephoto end (the unit movement position Pos7), from SP2. Then, the control circuit 90 instructs the motor drive circuit 92 to move the movable lens to the target step position SP4. Accordingly, the movable lens is moved to the step position SP4 and is stopped as shown in part (D) of FIG. 6.

Here, the threshold T2 is shorter than the minimum output time of a drive signal that is required to move the movable lens by the unit moving distance. When the control circuit 90 confirms that the duration T of the first on-operation is equal to or longer than the threshold T2, the movable lens is moved to the telephoto side toward the target step position SP2 at that time. The control circuit 90 extends the output time of the drive signal, which is set at that time by the motor drive circuit 92, without waiting for the ending of the movement of the movable lens to the step position SP2. That is, the control circuit 90 extends the output time of the drive signal by the output time of a drive signal required to move the movable lens to the step position SP4, which is a new target, from the current target step position SP2 (five times the minimum output time). Accordingly, the target step position is changed while the movable lens continues to move.

In the description of parts (A) and (D) of FIG. 6, the control circuit 90 has been adapted to start the movement of the movable lens to the telephoto side without waiting for the ending of the first on-operation. However, the movable lens may not be moved until the confirmation of whether or not at least the on-operation is a long push on-operation (whether or not the duration T is equal to or longer than the threshold T2), and the movable lens may start to be moved to the step position corresponding to each on-operation after the confirmation of whether or not the on-operation is a long push on-operation.

Further, also in cases in which the current step position of the movable lens is SP2 and SP3, the movable lens is moved to the step position SP4, which is provided at the telephoto end, by the same long push on-operation.

According to the operation described with reference to part (D) of FIG. 6, it is possible to move the movable lens to the step position SP4, which is provided at the telephoto end, from an arbitrary position by one on-operation.

Next, a case in which the number N of repetitions of the on-operation of the telephoto-side switch 79T is 2 and normal on-operations are performed as the repeated on-operations will be described. As shown in part (B) of FIG. 6, the current step position of the movable lens is SP1 (the unit movement position Pos0) and is stopped. At this time, the telephoto-side switch 79T is subjected to two repeated normal on-operations having duration T shorter than the threshold T2 and the number N of repetitions becomes 2.

In this case, when detecting the first on-operation, the control circuit 90 sets the number N of repetitions to 1 at that time. Then, the control circuit 90 determines the step position SP2 (the unit movement position Pos2), which is close to the telephoto side from the current step position SP1 by one step corresponding to the number N of repetitions, as the target step position. When the control circuit 90 determines the step position SP2 as the target step position, the control circuit 90 instructs the motor drive circuit 92 to move the movable lens to the target step position SP2 without waiting for the ending of the first on-operation.

Subsequently, when detecting the second repeated on-operation, the control circuit 90 changes the number N of repetitions to 2 at that time. Then, the control circuit 90 changes the target step position to the step position SP3 (the unit movement position Pos5) that is close to the telephoto side from the step position SP1, which is obtained when the control circuit 90 detects the first on-operation, by two steps corresponding to the number N of repetitions. After that, the control circuit 90 instructs the motor drive circuit 92 to move the movable lens to the target step position SP3. Accordingly, the movable lens is moved to the step position SP3 and is stopped as shown in part (B) of FIG. 6.

Also in a case in which the current step position of the movable lens is SP2, the movable lens is moved to the step position SP4, which is close to the telephoto side by two steps, by the same on-operation of which the number N of repetitions is 2. Further, in a case in which the current step position of the movable lens is SP3, the second on-operation is ineffective as described above but the first on-operation is effective. Accordingly, the movable lens is moved to the step position SP4 that is provided at the telephoto end.

In a case in which the first on-operation is a long push on-operation, the second on-operation is ineffective and the movable lens is moved to the step position SP4, which is provided at the telephoto end, as in part (D) of FIG. 6. Further, in a case in which the second on-operation is a long push on-operation, it is regarded that a normal on-operation is performed (it is regarded that only the duration T of the first on-operation is considered). Also in a case in which the second on-operation is a long push on-operation, the movable lens may be moved to the step position SP4, which is provided at the telephoto end, as in part (D) of FIG. 6. Furthermore, in a case in which the number N of repetitions is 2, the first long push on-operation may be regarded as a normal on-operation.

Moreover, when detecting the first on-operation, the control circuit 90 has been adapted to start the movement of the movable lens to the telephoto side without waiting for the ending of the first on-operation as described above. However, the movable lens may not be moved until the confirmation of the number N of repetitions, and may start to be moved to the step position corresponding to the number N of repetitions after the confirmation of the number N of repetitions.

According to the operation described with reference to part (B) of FIG. 6, the movable lens is not further moved to the telephoto side through the on-operation of the telephoto-side switch 79T by two steps after the movement of the movable lens to the telephoto side by one step, and it is possible to move the movable lens to the telephoto side by two steps through one continuous on-operation.

Next, a case in which the number N of repetitions of the on-operation of the telephoto-side switch 79T is 3 and normal on-operations are performed as the repeated on-operations will be described. As shown in part (C) of FIG. 6, the current step position of the movable lens is SP1 (the unit movement position Pos0) and is stopped. At this time, the telephoto-side switch 79T is subjected to three repeated normal on-operations having duration T shorter than the threshold T2 and the number N of repetitions becomes 3.

In this case, when detecting the first on-operation (a high-level voltage signal), the control circuit 90 sets the number N of repetitions to 1 at that time. Then, the control circuit 90 determines the step position SP2 (the unit movement position Pos2), which is close to the telephoto side from the current step position SP1 by one step corresponding to the number N of repetitions, as the target step position. When the control circuit 90 determines the step position SP2 as the target step position, the control circuit 90 instructs the motor drive circuit 92 to move the movable lens to the target step position SP2 without waiting for the ending of the first on-operation.

Subsequently, when detecting the second repeated on-operation, the control circuit 90 changes the number N of repetitions to 2 at that time. Then, the control circuit 90 changes the target step position to the step position SP3 (the unit movement position Posy) that is close to the telephoto side from the step position SP1, which is obtained when the control circuit 90 detects the first on-operation, by two steps corresponding to the number N of repetitions. After that, the control circuit 90 instructs the motor drive circuit 92 to move the movable lens to the target step position SP3.

Further, when detecting the third repeated on-operation, the control circuit 90 changes the number N of repetitions to 3 at that time. Then, the control circuit 90 changes the target step position to the step position SP4 (the unit movement position Pos7) that is close to the telephoto side from the step position SP1, which is obtained when the control circuit 90 detects the first on-operation, by three steps corresponding to the number N of repetitions. After that, the control circuit 90 instructs the motor drive circuit 92 to move the movable lens to the target step position SP4. Accordingly, the movable lens is moved to the step position SP4 and is stopped as shown in part (C) of FIG. 6.

In cases in which the current step position of the movable lens is SP2 and SP3, each of the second on-operation and the first on-operation is ineffective as described above but the on-operation performed before the second on-operation and the first on-operation is effective. Accordingly, the movable lens is moved to the step position SP4 that is provided at the telephoto end.

In a case in which the first on-operation is a long push on-operation as in the case in which the number N of repetitions is 2, the second or later on-operation is ineffective and the movable lens is moved to the step position SP4, which is provided at the telephoto end, as in part (D) of FIG. 6. Further, in a case in which the second or later on-operation is a long push on-operation, it is regarded that a normal on-operation is performed (it is regarded that only the duration T of the first on-operation is considered). Also in a case in which the second or later on-operation is a long push on-operation, the movable lens may be moved to the step position SP4, which is provided at the telephoto end, as in part (D) of FIG. 6. Furthermore, in a case in which the number N of repetitions is 3, the first long push on-operation may be regarded as a normal on-operation.

According to the operation described with reference to part (C) of FIG. 6, the movable lens is not moved to the telephoto side by three steps through the on-operation of the telephoto-side switch 79T, which is performed whenever the movable lens is moved to the telephoto side by one step, and it is possible to move the movable lens to the telephoto side by three steps through one continuous on-operation.

As described with reference to parts (A) to (C) of FIG. 6, the on-operation having the number N of repetitions means that the movable lens is moved by steps of which the number is the same as the number N of repetitions. Since the number of the step positions is four (SP1 to SP4) in this embodiment, an on-operation of which the number N of repetitions is 4 or more is not effective. However, the number of step positions can be arbitrarily set and changed, and the effective number N of repetitions also varies according to the number of step positions.

Next, a case in which the first on-operation of the telephoto-side switch 79T is performed when the movable lens is being moved to the telephoto side will be described. As shown in part (E) of FIG. 6, it is regarded that an on-operation of which the number N of repetitions is 2 is performed and the movable lens is moved to the telephoto side toward the step position SP3 as in part (B) of FIG. 6. In this case, the same processing as processing to be described below will be performed if the movable lens is being moved to the telephoto side.

In this state, it is regarded that the telephoto-side switch 79T is subjected to the first normal on-operation or the first long push on-operation. The first normal on-operation or the first long push on-operation means an on-operation that is performed after the duration of an off-operation becomes equal to or longer than the threshold T1 as described above.

In this case, when detecting the first on-operation (a high-level voltage signal), the control circuit 90 changes the target step position to the step position SP4, which is provided at the telephoto end, from a previous target step position. Then, the control circuit 90 instructs the motor drive circuit 92 to move the movable lens to the target step position SP4. Accordingly, the movable lens is moved to the step position SP4 and is stopped as shown in part (E) of FIG. 6.

According to the operation described with reference to part (E) of FIG. 6, the movement of the movable lens can be easily switched to the movement of the movable lens to the step position SP4 even when the movable lens is being moved to a step position other than the step position SP4 that is provided at the telephoto end.

Next, a case in which the telephoto-side switch 79T is subjected to the on-operation of the wide-side switch 79W, which is a reverse operating unit, when the movable lens is being moved to the telephoto side will be described. Three aspects, that is, first to third aspects will be described below, but any one of the aspects may be employed.

The first aspect will be described. As shown in part (F) of FIG. 6, it is regarded that an on-operation of the telephoto-side switch 79T of which the number N of repetitions is 3 is performed and the movable lens is moved to the telephoto side toward the step position SP4 from the step position SP1 as in part (C) of FIG. 6. In this case, the same processing as processing to be described below will be performed if the movable lens is being moved to the telephoto side.

In this state, it is regarded that the wide-side switch 79W is subjected to the first normal on-operation or the first long push on-operation.

In this case, when detecting the on-operation, the control circuit 90 keeps the target step position at the current target step position, that is, the step position SP4 in an example of FIG. 6(F) and stands by until the movable lens reaches the step position SP4.

Then, when the movable lens reaches the target step position SP4, the control circuit 90 determines a step position, which is obtained at the time of the start of the movement of the movable lens when the control circuit 90 detects the on-operation of the wide-side switch 79W, that is, the step position SP1 in an example of part (F) of FIG. 6, as a target step position. After that, the control circuit 90 instructs the motor drive circuit 92 to move the movable lens to the target step position SP1. Accordingly, after being moved to the step position SP4 as shown in part (F) of FIG. 6, the movable lens is moved to the step position SP1, which is an original step position before movement, and is stopped.

According to the operation described with reference to part (F) of FIG. 6, it is possible to return the movable lens to the original position by performing the on-operation of the wide-side switch 79W when the movable lens is moved to the telephoto side by the on-operation of the telephoto-side switch 79T.

Next, a second aspect will be described. As shown in part (G) of FIG. 6, it is regarded that an on-operation of the telephoto-side switch 79T of which the number N of repetitions is 3 is performed and the movable lens is moved to the telephoto side toward the step position SP4 from the step position SP1 as in part (F) of FIG. 6 (part (C) of FIG. 6). In this case, the same processing as processing to be described below will be performed if the movable lens is being moved to the telephoto side.

In this state, it is regarded that the wide-side switch 79W is subjected to the first normal on-operation or the first long push on-operation.

In this case, when detecting the on-operation, the control circuit 90 keeps the target step position at the current target step position, that is, the step position SP4 in an example of part (G) of FIG. 6 and stands by until the movable lens reaches the step position SP4.

Then, when the movable lens reaches the target step position SP4, the control circuit 90 determines the step position SP3, which is close to the wide side from the target step position SP4 by one step, as a target step position. After that, the control circuit 90 instructs the motor drive circuit 92 to move the movable lens to the target step position SP3. Accordingly, after being moved to the step position SP4 as shown in part (G) of FIG. 6, the movable lens is moved to the step position SP3, which is moved to the wide side by one step, and is stopped.

According to the operation described with reference to part (G) of FIG. 6, it is possible to return the movable lens to the wide side by one step from the target step position, which is obtained when the movable lens is moved to the telephoto side, by performing the on-operation of the wide-side switch 79W when the movable lens is moved to the telephoto side by the on-operation of the telephoto-side switch 79T.

Next, a third aspect will be described. As shown in part (H) of FIG. 6, it is regarded that an on-operation of the telephoto-side switch 79T of which the number N of repetitions is 3 is performed and the movable lens is moved to the telephoto side toward the step position SP4 from the step position SP1 as in parts (F) and (G) of FIG. 6 (part (C) of FIG. 6). In this case, the same processing as processing to be described below will be performed if the movable lens is being moved to the telephoto side.

In this state, it is regarded that the wide-side switch 79W is subjected to the first normal on-operation or the first long push on-operation.

In this case, when detecting the on-operation, the control circuit 90 keeps the target step position at the current target step position, that is, the step position SP4 in an example of FIG. 6(H) and stands by until the movable lens reaches the step position SP4.

Then, when the movable lens reaches the target step position SP4, the control circuit 90 determines a step position, which is closest to the wide side from the position of the movable lens obtained when the control circuit 90 detects the on-operation of the wide-side switch 79W, that is, the step position SP2 in an example of part (H) of FIG. 6 as a target step position. After that, the control circuit 90 instructs the motor drive circuit 92 to move the movable lens to the target step position SP2. Accordingly, after being moved to the step position SP4 as shown in FIG. 6(H), the movable lens is moved to the step position SP2 and is stopped.

According to the operation described with reference to part (H) of FIG. 6, it is possible to set the movable lens to substantially the same position as a position, which is obtained when the on-operation of the wide-side switch 79W is performed, by performing the on-operation of the wide-side switch 79W when the movable lens is moved to the telephoto side by the on-operation of the telephoto-side switch 79T.

The movable lens does not return to a step position that is obtained when the on-operation of the wide-side switch 79W is performed after the movable lens is moved to a target step position that is obtained when the movable lens is moved to the telephoto side; and the movable lens may be stopped at either position (a step position or a unit movement position) of the position of the movable lens, which is obtained when the on-operation of the wide-side switch 79W is performed, and a target step position, which is obtained at that time, and may return to the wide side.

The on-operation of the telephoto-side switch 79T in a case in which the movable lens stops and the on-operation of the telephoto-side switch 79T or the wide-side switch 79W in a case in which the movable lens is moved to the telephoto side have been described above. The on-operation of the wide-side switch 79W in a case in which the movable lens stops and the on-operation of the wide-side switch 79W or the telephoto-side switch 79T in a case in which the movable lens is moved to the wide side are completely the same as described above except that the moving direction of the movable lens is different.

The movable lens (the first and second movable lenses 22 and 23) of the imaging lens unit 11 (the objective optical system) of the imaging section 10 of the endoscope 60 has been moved by the drive of the DC motor in the above-mentioned embodiment. However, the movable lens may be moved by a piezoelectric actuator using a piezoelectric element, and may be moved by a stepping motor. Further, a mechanism for moving the movable lens may also not be a mechanism using a cam mechanism as in this embodiment.

Further, the invention may not relate to a movable lens for a variable zoom magnification, and can be applied to, for example, the control (operation) of an arbitrary movable lens, such as a movable lens for a variable focus.

EXPLANATION OF REFERENCES

10: imaging section
14: imaging lens
11: imaging lens unit
12: image pickup unit
15: lens moving unit
21: first stationary lens
21, 24: stationary lens
22: first movable lens
23: second movable lens
24: second stationary lens
25: camshaft
42: solid image pickup element
59: endoscope system
60: endoscope
61: processor device
62: light source device
66: insertion part
66a: tip portion
67: hand operation unit
79: zoom switch
79T: telephoto-side switch
79W: wide-side switch
80: motor
81: monitor
90: control circuit
92: motor drive circuit
94: zoom position detecting unit
96: non-volatile memory
100: main CPU

What is claimed is:

1. An endoscope apparatus comprising:
a movable lens that forms an objective optical system of an endoscope;
a lens drive unit that electrically drives the lens to one step position among a plurality of step positions;
an operating unit that outputs operation signals corresponding to an on-operation and an off-operation of an operator; and
a lens control unit that is configured to detect the duration of the on-operation, which is obtained when the on-operation is performed, and the number of repetitions of the on-operation, which is obtained when the on-operation and the off-operation are continuously repeated, on the basis of the operation signal, determine a step position to which the lens is to be moved on the basis of the detected duration of the on-operation and the detected number of repetitions of the on-operation and give a drive instruction for moving the lens to the step position that is determined by the lens control unit to the lens drive unit,
wherein the lens control unit gives the drive instruction to move the movable lens by plural steps through one continuous two or more on-operations.

2. The endoscope apparatus according to claim 1,
wherein if the on-operation is performed when the on-operation, which is performed after the duration of the off-operation becomes equal to or longer than a threshold T1, is defined as a first on-operation, the number of repetitions of the on-operation is defined as 1, and the duration of the off-operation performed after the on-operation is shorter than the threshold T1, the lens control unit increases the number of repetitions of the on-operation by 1.

3. The endoscope apparatus according to claim 2,
wherein when the lens control unit detects the first on-operation at the time of stopping of the lens, the lens control unit moves the lens to a step position spaced apart from a step position, which is obtained when the lens is stopped, in a moving direction, which is predetermined so as to correspond to the operating unit, by a step corresponding to the number of repetitions of the on-operation including the detected first on-operation after starting to move the lens in the moving direction.

4. The endoscope apparatus according to claim 3,
wherein when the lens control unit detects the first on-operation at the time of stopping of the lens, the lens control unit moves the lens to a step position that is provided at an end in a moving direction predetermined so as to correspond to the operating unit by the detection of the first on-operation after starting to move the lens in the moving direction in a case in which the duration of the first on-operation becomes equal to or longer than a threshold T2.

5. The endoscope apparatus according to claim 4,
wherein if the lens control unit detects the first on-operation when moving the lens in the moving direction that is predetermined so as to correspond to the operating unit, the lens control unit moves the lens to a step position that is provided at an end in the moving direction.

6. The endoscope apparatus according to claim 4, further comprising:
a reverse operating unit that outputs operation signals corresponding to an on-operation and an off-operation of an operator,
wherein if the lens control unit detects an on-operation performed by the reverse operating unit when moving the lens in a moving direction that is predetermined so as to correspond to the operating unit, the lens control unit moves the lens to a step position that is obtained at the time of the start of the movement of the lens.

7. The endoscope apparatus according to claim 3,
wherein if the lens control unit detects the first on-operation when moving the lens in the moving direction that is predetermined so as to correspond to the operating unit, the lens control unit moves the lens to a step position that is provided at an end in the moving direction.

8. The endoscope apparatus according to claim 3, further comprising:
a reverse operating unit that outputs operation signals corresponding to an on-operation and an off-operation of an operator,
wherein if the lens control unit detects an on-operation performed by the reverse operating unit when moving the lens in a moving direction that is predetermined so as to correspond to the operating unit, the lens control unit moves the lens to a step position that is obtained at the time of the start of the movement of the lens.

9. The endoscope apparatus according to claim 2,
wherein when the lens control unit detects the first on-operation at the time of stopping of the lens, the lens control unit moves the lens to a step position that is provided at an end in a moving direction predetermined so as to correspond to the operating unit by the detection of the first on-operation after starting to move the lens in the moving direction in a case in which the duration of the first on-operation becomes equal to or longer than a threshold T2.

10. The endoscope apparatus according to claim 9,
wherein if the lens control unit detects the first on-operation when moving the lens in the moving direction that is predetermined so as to correspond to the operating unit, the lens control unit moves the lens to a step position that is provided at an end in the moving direction.

11. The endoscope apparatus according to claim 9, further comprising:
a reverse operating unit that outputs operation signals corresponding to an on-operation and an off-operation of an operator,
wherein if the lens control unit detects an on-operation performed by the reverse operating unit when moving the lens in a moving direction that is predetermined so as to correspond to the operating unit, the lens control unit moves the lens to a step position that is obtained at the time of the start of the movement of the lens.

12. The endoscope apparatus according to claim 9,
wherein the threshold T2 is longer than 0 and shorter than a minimum output time of a drive signal that is required to move the movable lens by a unit moving distance.

13. The endoscope apparatus according to claim 2,
wherein if the lens control unit detects the first on-operation when moving the lens in the moving direction that is predetermined so as to correspond to the operating unit, the lens control unit moves the lens to a step position that is provided at an end in the moving direction.

14. The endoscope apparatus according to claim 13, further comprising:

a reverse operating unit that outputs operation signals corresponding to an on-operation and an off-operation of an operator, wherein if the lens control unit detects an on-operation performed by the reverse operating unit when moving the lens in a moving direction that is predetermined so as to correspond to the operating unit, the lens control unit moves the lens to a step position that is obtained at the time of the start of the movement of the lens.

15. The endoscope apparatus according to claim 2, further comprising:
a reverse operating unit that outputs operation signals corresponding to an on-operation and an off-operation of an operator, wherein if the lens control unit detects an on-operation performed by the reverse operating unit when moving the lens in a moving direction that is predetermined so as to correspond to the operating unit, the lens control unit moves the lens to a step position that is obtained at the time of the start of the movement of the lens.

16. The endoscope apparatus according to claim 1, wherein the lens drive unit is a unit that drives the lens by a DC motor.

17. The endoscope apparatus according to claim 1, wherein the operating unit is a unit that outputs an operation signal corresponding to an operation for pushing a switch as the on-operation.

18. The endoscope apparatus according to claim 1, wherein the lens control unit is configured to include a lookup table in which the step positions are associated with positions that are settable when the lens control unit moves the lens by a moving distance corresponding to the minimum unit by the drive instruction given to the lens drive unit, and move the lens to a target step position with reference to the lookup table.

19. The endoscope apparatus according to claim 1, wherein the lens is a lens for a variable zoom magnification of the objective optical system, and
the step position is a position of the lens for the setting of a predetermined zoom magnification.

20. An endoscope apparatus comprising:
a movable lens that forms an objective optical system of an endoscope;
a lens drive unit that electrically drives the lens to one step position among a plurality of step positions;
an operating unit that outputs operation signals corresponding to an on-operation and an off-operation of an operator;
a lens control unit that is configured to detect the duration of the on-operation, which is obtained when the on-operation is performed, and the number of repetitions of the on-operation, which is obtained when the on-operation and the off-operation are continuously repeated, on the basis of the operation signal, determine a step position to which the lens is to be moved on the basis of the detected duration of the on-operation and the detected number of repetitions of the on-operation and give a drive instruction for moving the lens to the step position that is determined by the lens control unit to the lens drive unit, and
a reverse operating unit that outputs operation signals corresponding to an on-operation and an off-operation of an operator, wherein if the on-operation is performed when the on-operation, which is performed after the duration of the off-operation becomes equal to or longer than a threshold T1, is defined as a first on-operation, the number of repetitions of the on-operation is defined as 1, and the duration of the off-operation performed after the on-operation is shorter than the threshold T1, the lens control unit increases the number of repetitions of the on-operation by 1, and wherein if the lens control unit detects an on-operation performed by the reverse operating unit when moving the lens in a moving direction, which is predetermined so as to correspond to the operating unit, to move the lens to a target step position, the lens control unit moves the lens to a step position, which is spaced apart from a target position in a direction opposite to the moving direction by one step, after moving the lens to the target step position.

21. An endoscope apparatus comprising:
a movable lens that forms an objective optical system of an endoscope;
a lens drive unit that electrically drives the lens to one step position among a plurality of step positions;
an operating unit that outputs operation signals corresponding to an on-operation and an off-operation of an operator;
a lens control unit that is configured to detect the duration of the on-operation, which is obtained when the on-operation is performed, and the number of repetitions of the on-operation, which is obtained when the on-operation and the off-operation are continuously repeated, on the basis of the operation signal, determine a step position to which the lens is to be moved on the basis of the detected duration of the on-operation and the detected number of repetitions of the on-operation and give a drive instruction for moving the lens to the step position that is determined by the lens control unit to the lens drive unit, and
a reverse operating unit that outputs operation signals corresponding to an on-operation and an off-operation of an operator, wherein if the on-operation is performed when the on-operation, which is performed after the duration of the off-operation becomes equal to or longer than a threshold T1, is defined as a first on-operation, the number of repetitions of the on-operation is defined as 1, and the duration of the off-operation performed after the on-operation is shorter than the threshold T1, the lens control unit increases the number of repetitions of the on-operation by 1, and wherein if the lens control unit detects an on-operation performed by the reverse operating unit when moving the lens in a moving direction, which is predetermined so as to correspond to the operating unit, to move the lens to a target step position, the lens control unit moves the lens to a step position closest to a position of the lens, which is obtained at the time of the detection of the on-operation performed by the reverse operating unit, in a direction opposite to the moving direction.

* * * * *